(12) United States Patent
Kline-Schoder et al.

(10) Patent No.: US 6,629,449 B1
(45) Date of Patent: Oct. 7, 2003

(54) BUBBLE MEASURING INSTRUMENT AND METHOD

(75) Inventors: Robert Kline-Schoder, Norwich, VT (US); Patrick J. Magari, Plainfield, NH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/113,645

(22) Filed: Mar. 26, 2002

Related U.S. Application Data

(62) Division of application No. 09/498,440, filed on Feb. 4, 2000, now Pat. No. 6,408,679.

(51) Int. Cl.[7] .................. G06K 9/00; G06F 15/00; G01N 21/89
(52) U.S. Cl. .............. 73/19.03; 73/53.01; 73/19.1; 356/243.2; 356/335; 382/133
(58) Field of Search .............. 73/19.03, 61.75, 73/61.71, 53.01, 19.01, 19.1; 382/141, 133; 356/243.2, 239.6, 335

(56) References Cited

U.S. PATENT DOCUMENTS

| | | | | |
|---|---|---|---|---|
| 4,689,986 A | * | 9/1987 | Carson et al. | 73/19.01 |
| 4,902,137 A | * | 2/1990 | Krieg et al. | 356/427 |
| 5,127,962 A | * | 7/1992 | Inoue et al. | 134/22.12 |
| 5,471,383 A | * | 11/1995 | Gobush et al. | 364/410 |
| 5,653,250 A | * | 8/1997 | Sigmund et al. | 137/7 |
| 5,675,071 A | * | 10/1997 | Cody et al. | 73/32 A |
| 5,918,272 A | * | 6/1999 | Snyder et al. | 73/61.42 |
| 5,930,740 A | * | 7/1999 | Mathisen | 702/152 |
| 6,116,516 A | * | 9/2000 | Ganan-Calvo | 239/8 |
| 6,197,835 B1 | * | 3/2001 | Ganan-Calvo | 516/10 |
| 6,252,980 B1 | * | 6/2001 | Schwartz et al. | 382/141 |
| 6,271,853 B1 | * | 8/2001 | Oxaal | 345/425 |

OTHER PUBLICATIONS

Dominique Cathignol et al., "Bubble Sizing with High Spatial Resolution", Jan. 1990, IEEE Transactions on Ultrasonics, Ferroelectrics, and Frequency Control; vol. 37, No. 01; pp. 30–37.*

* cited by examiner

*Primary Examiner*—Hezron Williams
*Assistant Examiner*—David J. Wiggins
(74) *Attorney, Agent, or Firm*—James M. Cate

(57) ABSTRACT

Method and apparatus are provided for a non-invasive bubble measuring instrument operable for detecting, distinguishing, and counting gaseous embolisms such as bubbles over a selectable range of bubble sizes of interest. A selected measurement volume in which bubbles may be detected is insonified by two distinct frequencies from a pump transducer and an image transducer, respectively. The image transducer frequency is much higher than the pump transducer frequency. The relatively low-frequency pump signal is used to excite bubbles to resonate at a frequency related to their diameter. The image transducer is operated in a pulse-echo mode at a controllable repetition rate that transmits bursts of high-frequency ultrasonic signal to the measurement volume in which bubbles may be detected and then receives the echo. From the echo or received signal, a beat signal related to the repetition rate may be extracted and used to indicate the presence or absence of a resonant bubble. In a preferred embodiment, software control maintains the beat signal at a preselected frequency while varying the pump transducer frequency to excite bubbles of different diameters to resonate depending on the range of bubble diameters selected for investigation.

14 Claims, 8 Drawing Sheets

BUBBLE MEASURING INSTRUMENT AND METHOD

This application is a division, Ser. No. 09/498,440, filed Feb. 4, 2000 which application was granted as U.S. Pat. No. 6,408,679 on Jun. 25, 2002.

ORGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates to apparatus and methods for measuring bubbles in fluids and tissues and, more specifically, to apparatus and methods for detecting, sizing, and counting gaseous emboli in a non-invasive manner.

2. Description of Prior Art

In-vivo measurement of the size and number of bubbles in fluids and tissues may be used to prevent, diagnose, and/or treat many potentially serious medical conditions such as, for example only, decompression sickness or stroke following cardiopulmonary bypass procedures. In-vitro or out of the body measurement of bubbles is also useful in connection with medical equipment that involves the flow of fluids into or out of the body. Emboli of various types may occur in the body for many medical reasons. Detecting and/or distinguishing gaseous emboli from other types of emboli is highly desirable so that appropriate medical management decisions can be made. Emboli may consist of formed elements such as blood clots, platelet aggregates, or other particulate matter such as pieces of atherosclerotic plaque or fat. Emboli may also consist of gas bubbles introduced to the blood vessels through injection, surgical techniques, cavitation at prosthetic valves, or decompression or compression to lower or higher atmospheric pressures.

In-vivo measurements of bubbles are especially useful with respect to decompression sickness. Decompression sickness poses a risk of serious injury or death to aviators, astronauts, divers, and others who are exposed to varying environmental pressure conditions. NASA, Air Force, Navy, and civilian personnel rely on pressure suits, controlled breathing mixtures, and operating procedures to maintain "acceptable" environmental conditions to prevent decompression sickness. These "acceptable" conditions are determined empirically, based on experimental observations of decompression sickness and its precursors. The symptoms of decompression sickness are attributed to the presence of gas bubbles, comprised mostly of nitrogen, in vascular and extravascular tissue. In vascular tissue, these bubbles can lodge or embolize in vessels in the pulmonary or systemic circulation systems, resulting in a range of pathology which is included in decompression sickness. These bubbles are formed due to local supersaturation of nitrogen upon reduction of ambient pressure or possibly upon warming from a hypothermic condition. The formation of bubbles and the onset of decompression sickness, which do not necessarily coincide, are highly variable and depend on a large range of factors including duration and magnitude of ambient pressure excursions, exercise, hydration, rate of change of pressure, hypoxia, temperature, age, infection, fitness, fatigue, previous injury, sex, and body fat.

In addition to decompression sickness, embolic events associated with the use of cardiopulmonary bypasses have been a serious concern. There are an estimated 700,000 cardiopulmonary bypass procedures performed annually in the U.S. In prospective studies of postoperative neurological dysfunction following cardiopulmonary bypass, the incidence rate is as high as 30% to 60%. The incidence of stroke following cardiopulmonary bypass is 1% to 5%. It is generally accepted that these effects are a consequence of microembolism, and/or compromise of cerebral blood flow. Emboli associated with cardiopulmonary bypass can be comprised of biological material, such as oxygen or nitrogen. The source of blood cell aggregates and thrombi is typically an activation of the thrombogenic cascade by blood interaction with a foreign surface, or they may be introduced with transfused blood. The sources of gaseous emboli include the blood oxygenation system and cavitation in the pumping systems.

Another major source of gaseous emboli is so-called "surgical air", which can be introduced during cardiotomy for procedures like valvular and septal repair in the heart. These bubbles are of particular concern, because they contain air (primarily nitrogen) and are much less soluble in blood and tissue than oxygen bubbles. "Surgical air" has also been associated with neurological dysfunction in major organ transplant surgeries, such as liver transplants.

Gaseous emboli can also be generated in the body as a result of cavitation associated with artificial heart valves. These devices also potentially create thrombotic emboli, and as a result there is a need for instrumentation which can distinguish between the two types of events to aid device development and to aid diagnosis.

An improved ability to monitor for vascular and extravascular bubbles would have a significant impact on the ability to prevent and minimize decompression sickness and embolic pathology. In particular, better data on the early occurrence of bubbles, their size, and their composition (gaseous/non-gaseous) will permit less restrictive operational and design criteria to be developed for the prevention of decompression sickness in astronauts, aviators, and divers by permitting direct observation of the important variable of bubble size during decompression events. Direct monitoring of operational personnel in high risk decompression sickness circumstances would provide a quantitative indication to provide much more accuracy as to their proximity to the onset of symptomatic decompression sickness.

Improved monitoring would aid in therapy, recovery, and survival of patients being treated for decompression sickness and gaseous embolism by providing the first quantitative information about the size of the bubbles which are giving rise to their pathology. It would be highly desirable to provide for direct monitoring of the presence and size of gaseous bubbles such as gaseous emboli during and after surgical procedures with high likelihood of emboli introduction, such as cardiopulmonary bypass, with the goal being a subsequent decrease in the rate of embolic complications.

More generally, improved monitoring would provide clinicians with early warning of the introduction, size, and composition of emboli, allowing for better informed therapeutic approaches to be used. As well, biomedical researchers would have an improved ability to classify and quantify emboli produced by artificial heart valves and cardiopulmonary bypass machines.

To date, the detection of emboli, both gaseous and non-gaseous, has been largely accomplished through the use of Doppler ultrasound. This technique tells the observer whether there are bubbles or emboli present and provides an indication as to how many are present based on the rate of detection. The Doppler technique is only able to detect emboli flowing with sufficient speed in large vessels, when the direction of motion of the flow and the orientation of the acoustic beam are in a restrictive range. Doppler techniques have virtually no ability to quantify the size of the bubbles, observe bubbles in non-vascular tissue or in slow flowing microvessels, and have limited usefulness in classifying emboli as gaseous or non-gaseous. These are serious limitations with regard to detection and classification of: (1) decompression sickness precursor bubbles, (2) emboli during surgical procedures, and (3) emboli generated by artificial heart valves.

The following patents disclose attempts to solve the above discussed difficult problems and related problems over the last two decades.

U.S. Pat. No. 5,441,051, issued Aug. 15, 1995, to Hileman et al., discloses a method and apparatus for ultrasonically detecting an embolus in blood flow, including an ultrasound transducer for transmitting ultrasound pulses into the blood flow being interrogated and receiving reflections from acoustic impedance changes in the body. The reflected signals are converted to an electronic signal representation which is subsequently processed to detect and classify emboli in the blood flow. A short duration, broad bandwidth ultrasound signal is used to preserve the polarity of the reflected signal. The polarity is then used to classify the emboli based on a positive or negative reflection coefficient. Emboli having a negative reflection coefficient are classified as either gaseous or fat particles, and emboli having a positive reflection coefficient are classified as solid particles. The emboli can be further classified based on the amplitude of the reflected signal, or designated features of the time waveform or FFT of the reflected signal.

U.S. Pat. No. 5,348,015, issued Sep. 20, 1994, to Moehring et al., discloses a noninvasive means for detecting, counting, and characterizing emboli moving through the arterial or venous circulation. An ultrasonic transducer is applied to the skin or other tissues of the subject at sites such as over the temporal bone on either side of the head of the subject, on the neck, on the chest, the abdomen, arm, leg, within the esophagus, or surgically exposed organs or blood vessels. Using standard ultrasonic Doppler techniques, Doppler-shifted signals are located which are proportional to the blood flow velocity in the blood vessel(s) of interest. Spectral analysis is performed on the received signal using the fast Fourier transform or other appropriate technique to determine the frequency components in the Doppler shift spectrum. Further analysis of the spectra is used to delineate and characterize Doppler shift signals due to blood from Doppler shift signals due to emboli having a variety of compositions.

U.S. Pat. No. 5,198,776, issued Mar. 30, 1993, to Kenneth L. Carr, discloses an apparatus and method for detecting the presence of incidental bubbles in liquid flowing in a tube. The system monitors the amplitude of microwave radiation reflected from the liquid and recognizes when that amplitude drops in a manner characteristic of the presence of a bubble.

U.S. Pat. No. 5,103,827, issued Apr. 14, 1992, to George H. Smith, discloses a method and apparatus for distinguishing ultrasound signals returned from bubbles and particles moving in a fluid from signals due to ultrasound transducer motion that monitors the receiving ultrasound signal for signals which are of much larger amplitude than the signals observed when no gas bubbles or particles are present. When a large amplitude event is detected, the maximum amplitude of the forward flow signal (that is, the positive frequency portion of the power spectrum) is compared to the maximum amplitude of the reverse flow signal (negative frequency portion of the power spectrum). If these maxima are significantly different in amplitude, the event is counted as a bubble. If the maximum amplitudes of the forward and reverse flow signals are comparable, the event is classified as a motion artifact. Displays of the spectra are marked whenever an event is counted as an air or particulate emboli so as to call attention to the event and, optionally, to generate an audible or visual alarm.

U.S. Pat. No. 4,689,986, issued Sep. 1, 1987, to Carson et al., discloses a system for detecting gas bubbles in a specimen utilizing a transducer which produces pulses, illustratively of ultrasonic acoustic energy, having predetermined frequency characteristics. A first pulse has an increasing frequency with time, and a second pulse has a decreasing frequency with time. Imaging arrangements, which may be formed of ultrasonic transducers, produce images of the region within the specimen after exposure to each such pulse. In one embodiment, a growth transducer array is utilized for dramatically increasing the size of the bubbles, which array is formed of a plurality of transducers which are moved with respect to the specimen and which have respective frequency characteristics over different frequency ranges. Thus, bubble radius is successively increased as each bubble is exposed to the acoustic energy from each such transducer within the growth transducer array. The invention of Carson et al. can be used to reduce the cavitation threshold of bubbles, particularly in the vicinity of tumors, or to increase the temperature in the bubble-containing region.

U.S. Pat. No. 4,657,756, issued April 14, 1987, to Rasor et al., discloses that microbubbles are formed in a liquid, e.g., blood in order to alter the transmission characteristics thereof to electromagnetic and sonic waves transmitted therethrough, by dissolving therein a solid particulate material, preferably as a suspension in a carrier liquid in which the particulate material is at least temporarily stable, the particles of which are substantially free of microbubbles and have a plurality of gas-filled voids in fluid communication with the surface of the particles and providing nuclei for microbubble formation and the ratio of the mass of the particles to the volume of gas in the voids is sufficient to render the liquid in which the particulate material is dissolved supersaturated with respect to the gas in the voids in the area of the liquid surrounding the microbubbles when they are formed.

U.S. Pat. No. 4,483,345, issued Nov. 20, 1984, to Hirohide Miwa, discloses a system for measuring from the outside of a living body the pressure within the heart of the pressure of any portion which does not allow a measurement by the direct insertion of a pressure measuring sensor. This system provides a method of measuring the pressure of the object by generating fine bubbles through cavitation, applying a low-frequency ultrasonic wave to the medium, and then detecting the bubbles which are generated with a system for detecting the high or low-frequency harmonics due to the bubbles or a higher frequency ultrasonic wave applied to the medium.

U.S. Pat. No 4,459,853, issued Jul. 17, 1984, to Miwa et al., discloses a probe which comprises a plurality of ultrasonic transducer elements, and is so arranged as to be capable of simultaneously transmitting and receiving ultrasonic beams of plural frequencies. Means is provided for changing the shapes of the effective acoustic field of the ultrasonic beams of each a predetermined number of frequencies by selectively operating the ultrasonic transducer elements or interchanging transducers. The shapes of the effective acoustic fields of the ultrasonic beams of the plural frequencies are made substantially coincident in accordance with the range of distance from the probe. Thereby, the measuring of the tissue or the like with coincident shaped beams of plural frequencies can be realized.

U.S. Pat. No. 4,290,432, issued Sep. 22, 1981, to Stephen Daniels, discloses a decompression bubble detector which comprises a pulsed ultra-sound transmitter/receiver which is scanned across a cross-section of tissue and the total number of pulse echoes received in a preselected time interval is recorded. Changes in the total number of pulse echoes recorded in successive time intervals are used to monitor the decompression. A single transducer is scanned by means of a driven eccentric cam and a cam follower. A sin/cos potentiometer generates a signal related to the angular position of the transducer connected to a delay so that pulse counting can be arranged to coincide with the passage of the transducer across the target.

U.S. Pat. No. 4,152,928, issued May 8, 1979, to Richard A. Roberts, discloses a system utilizing a bank of frequency staggered band-pass filters spanning the range in which fat emboli are known to occur which is used for the early detection of fat emboli in blood.

U.S. Pat. No. 4,015,464, issued Apr. 5, 1977, to Miller et al., discloses an apparatus for sensing particles in a fluid medium which comprises an ultrasonic resonant cavity for containing a fluid medium. A first transducer on one side of the cavity continuously propagates thereacross ultrasonic compressional waves whose phase and amplitude are perturbed by the presence of particles in the fluid medium. A second transducer positioned on the opposite side of the cavity from the first transducer substantially parallel to and in registry therewith receives the ultrasonic waves and converts them to rf electric waves of the same frequency, the $r_f$ electric waves having their phases and amplitudes modulated in response to any perturbations in the ultrasonic waves. The rf waves are amplified and fed back to the first transducer thereby to establish an oscillatory circuit. An attenuator in the oscillatory circuit causes its operation to be marginally oscillatory whereby small changes in the amplitude of the rf waves caused by any perturbations in the ultrasonic waves produce relatively large changes in the amplitude thereof. A detector responsive to perturbations in the rf wave demodulates the amplified rf wave to produce signals indicative of the presence of particles in the fluid medium. Thus, enhanced sensitivity to small changes in the ultrasonic properties of the fluid medium caused by the presence of particles therein is achieved.

U.S. Pat. No. 3,974,683, issued Aug. 17, 1976, to Roger Martin, discloses an apparatus for ultrasonic testing which comprises a pulsed ultrasonic transducer, means for detecting echoes from bubbles in a liquid and means for determining the volume of the bubbles.

U.S. Pat. No. 3,974,681, issued Aug. 17, 1976, to Jerry Namery, discloses the mode of operation by ultrasonic through-transmission and a detector preferably employed for detecting air bubbles in intravenous feeding tubes to prevent air embolism. Transmission of sound from the transmitter, via the sensor head, to the receiver of the detector is dependent upon the existence of a fluid within the tubing. Acoustic losses, operating frequency, and the distance between transmitter and receiver are optimized to permit constructive-interference of energy transmitted to and reflected from the receiver, resulting in a partial standing wave as in a resonant cavity. If an air bubble passes through the sensor head, a large acoustic discontinuity occurs, causing ultrasound to scatter and reflect from its normal path. These losses allow little ultrasonic energy to couple to the receiver. The sensor head includes spaced oppositely disposed cylindrical sound pipe segments having facing tubing accommodating recesses, and respectively connecting to the transmitter and receiver. Sound pipe segments have a markedly higher refractive index in comparison with the feeding tubing and its liquid contents causing ultrasound energy to focus towards the center of the feeding tube, thereby yielding greatest sensitivity to transmission losses through the fluid within the feeding tube.

The above cited prior art does not provide an in vivo means for sizing and counting the bubbles of any particular specific size or for selectable ranges of bubble sizes as is desirable for many medical purposes. Consequently, there is a strong need within the biomedical research community for the noninvasive, bubble sizing instrument disclosed herein. Those skilled in the art have long sought and will appreciate the present invention that addresses these and other problems.

SUMMARY OF THE INVENTION

A method is provided for monitoring a selected volume for gaseous bubbles comprising steps such as producing a first acoustic signal at a first frequency and producing a second acoustic signal having a second frequency higher than the first frequency. The second acoustic signal is produced in a pulsed mode such that the pulses are produced at a repetition frequency. The first frequency and the repetition frequency are selectable to produce a beat signal with a selected frequency. The beat signal is monitored at the selected frequency to detect the bubbles.

The first frequency and the repetition frequency are selected such that the repetition frequency is not equal to the first frequency divided by an integer. The first frequency may preferably be varied to monitor a range of bubble sizes. As the first frequency is varied, the repetition frequency may be continually adjusted by altering the pulsed mode operation accordingly as needed to maintain the beat signal at the selected beat signal frequency.

The second frequency is preferably kept constant. When using a single transducer, the transducer may be monitored for the beat signal between pulses of the second acoustic signal.

A high pass filter may be used to eliminate signals below the selected frequency for detecting the beat signal. As well, a low pass filter may be used to eliminate signals above the selected frequency for detecting the beat signal.

The first and second acoustic signals are directed at the selected volume in which bubbles are to be measured. A signal response is detected from the selected volume. The first frequency and the repetition frequency are preferably controlled such that the repetition frequency is not equal to the first frequency divided by an integer as the first frequency varies. A beat signal is detected related to the presence of a bubble in the selected volume. The repetition frequency is preferably controlled to maintain the beat signal at a constant beat frequency as the first frequency varies.

A rate for varying the first frequency may be selected such that the rate is related to the time required for monitoring the range of bubble sizes to be detected. Selecting the rate for varying the first frequency further comprises selecting a frequency sweep increment such that the pump frequency is incremented in steps through a range of frequencies related to the range of bubble sizes to be detected. The bubble size may be determined based on the first frequency.

An apparatus for monitoring bubbles in a selected volume comprises a pump transducer and a controller for the pump transducer operable for producing a signal at a first frequency from the pump transducer. The first frequency may be selectable over a range of frequencies. An image transducer is provided and a reference signal generator is used for producing a reference signal at a second frequency higher than the first frequency. A pulser produces a pulsed signal output from the image transducer at the second frequency. A receiver may be used for detecting a return signal from the image transducer and a multiplier may be used for multiplying the return signal with the reference signal to produce a multiplier output signal.

A first low pass filter is preferably used for filtering the multiplier output signal to produce a first filtered signal. A sample and hold circuit receives the first filtered signal to further detect a beat signal. A second lowpass filter and a highpass filter may be used for producing the beat signal. A level detector which may be software controlled may be used for detecting a bubble from the amplitude of the beat signal response. A pulser controller may be used for controlling a repetition frequency of the pulsed signal output. The pulser controller is preferably software controlled for selecting the repetition frequency. The pulser controller may vary the repetition frequency based on the first frequency. Preferably, the pulser controller is programmed for varying the repetition frequency to maintain a constant frequency of a beat signal contained in the return signal.

Preferably a video bubble sizing apparatus is provided for verifying operation of the ultrasonic bubble monitor in vitro and comprises a video camera with software for capturing video images, a sight tube containing bubbles, and a strobe for producing separate video frames showing bubbles. A video monitor may be used for viewing the separate video frames with bubbles therein. The software may be operable for providing statistically independent frames such that the same bubble is not measured twice in the separate video frames.

A tissue phantom is preferably used for simulating in-vivo bubbles to be observed ultrasonically in a tube through which bubbles are entrained. A housing is provided having a covering of synthetic material to simulate skin. A rod may be disposed within the housing for simulating bone; and a gel may be disposed within the housing for simulating tissue. The video system for viewing bubbles in the tube verifies results of the in-vitro bubbles observed ultrasonically.

One object of the present invention is to provide an improved instrument and method for non-invasively monitoring bubbles.

Another object of the present invention is to size bubbles over a range that includes at least the gaseous emboli in the range of 40 $\mu$m to 400 $\mu$m although detection of gaseous emboli outside this range may also be useful and may be accomplished using the present invention.

Yet another objective of the present invention is to verify the bubble monitoring instrument performance by providing an independent means for measuring the size of bubble populations.

Yet another objective of the present invention is to provide an in-vitro method to test operation of the present invention in a manner that simulates in-vivo operation and provides for verification of operation and instrument accuracy.

Any listed objects, features, and advantages are not intended to limit the invention or claims in any conceivable manner but are intended merely to be informative of some of the objects, features, and advantages of the present invention. In fact, these and yet other objects, features, and advantages of the present invention will become apparent from the drawings, the descriptions given herein, and the appended claims.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

BRIEF DESCRIPTION OF PREFERRED EMBODIMENTS

Figure 1:
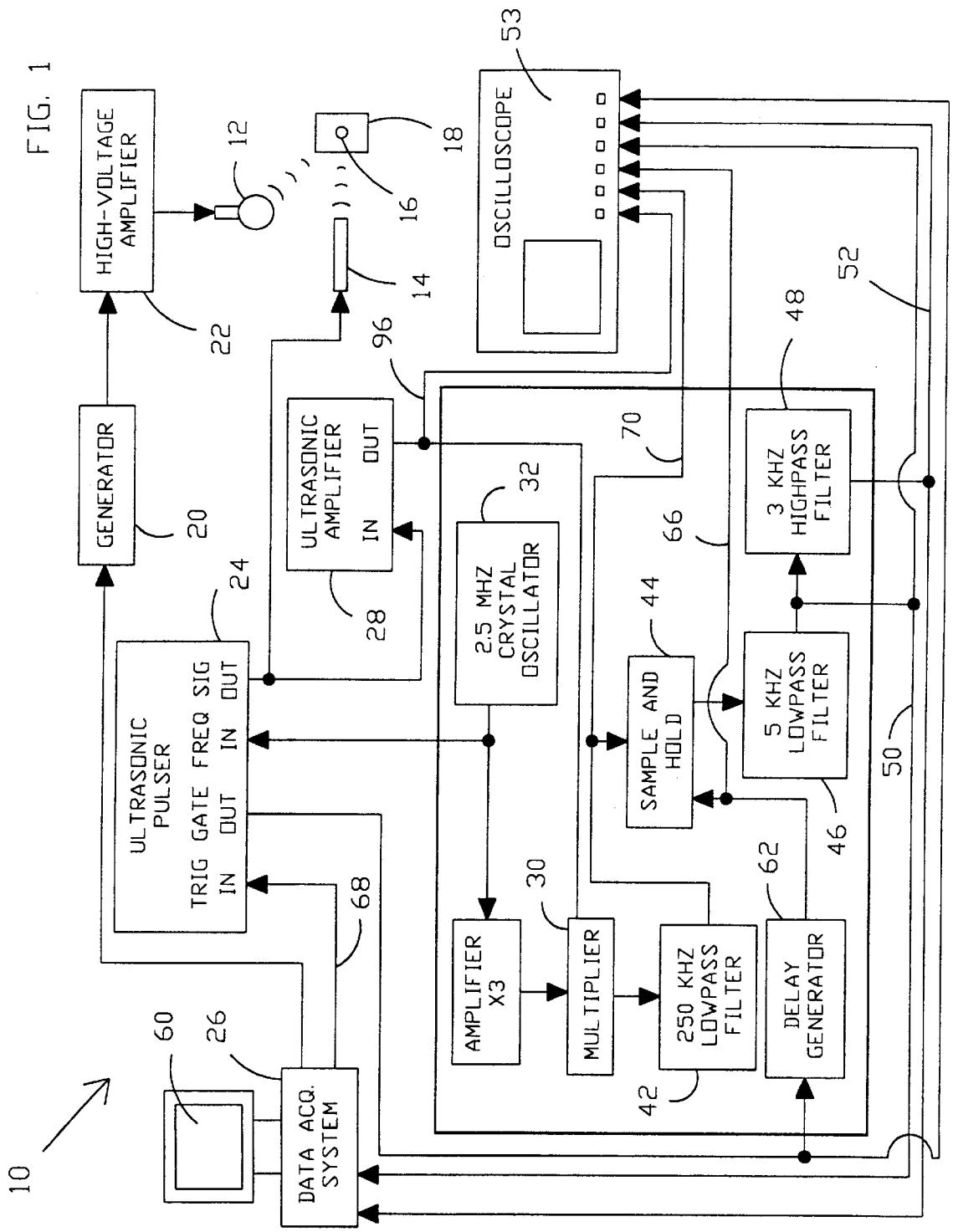
FIG. 1 is a block diagram for a bubble measuring instrument in accord with the present invention.

Referring now to the drawings, and more particularly to FIG. 1, the present invention discloses a non-invasive, in-vivo instrument 10 for detecting, classifying and sizing gaseous emboli. Gaseous emboli which result in decompression sickness (DCS) pose a serious risk of injury to aviators, astronauts, divers and other individuals who are exposed to varying environmental pressure. Gaseous emboli are also a serious complication of cardiopulmonary bypass, surgical air introduced during cardiotomy, and heart valve replacement resulting in cavitation bubbles. Instrument 10 will significantly aid research on DCS and other gaseous embolic events by providing a new capability to distinguish between gaseous and thrombotic emboli, and to size gaseous emboli in a noninvasive way.

The fundamental basis of the instrument is the use of ultrasound to excite the resonant behavior of the gaseous emboli. The resonant behavior is a function of the gaseous bubble diameter and is well characterized analytically so that little or no instrument calibration is required. Nongaseous emboli do not display the same resonant characteristics as gaseous emboli, thus providing a means for distinguishing between the two types of emboli. Instrument 10 consists of low-frequency pump transducer 12 to excite the fundamental vibration mode of the bubbles as indicated at 16, high-frequency imaging transducer 14 to observe the resonance, and signal processing and analysis equipment discussed in more detail hereinafter.

To interrogate a selected measurement volume 18 for a particular bubble size, a pump frequency is selected, corresponding to a specific bubble size, and the field is simultaneously insonified with the pump signal and the image signal. Because the bubbles act as nonlinear mixers, a high-frequency return signal is produced with sidebands at plus and minus the pump frequency, if and only if, there is a gaseous bubble with a fundamental resonant frequency corresponding to the pump transducer frequency. The range of bubble sizes of interest may be scanned by varying the pump frequency over the appropriate range. For various reasons, we operate the instrument in a pulse/echo mode which adds several complications to the signal processing, but the benefits of operating in this mode are significant.

Instrument 10 exploits the resonant behavior of gaseous emboli. This behavior is a strong function of bubble diameter and is well predicted theoretically. As a consequence, by basing the instrument on the resonant behavior of the bubbles, it is possible to have an instrument which provides excellent resolution and requires little or no calibration. The theoretical relationships between bubble diameter, resonant frequency, and damping of the volume mode for a bubble of given diameter have been known for some time and are given by:

$$f_0 = 2\pi \sqrt{\frac{3\gamma(P_0 + 2\sigma/R_0) - 2\sigma/R_0}{\rho R_0^2}}$$

where,
$f_0$=first resonant frequency,
$R_0$=nominal bubble radius,
$\rho$=suspending mass density,
$P_0$=ambient pressure, and
$\sigma$=surface tension.

From this relationship, it can be determined that bubbles having a diameter in the range of 40 μm to 400 μm have resonant frequencies in the range of 200 kHz to 20 kHz, respectively.

In accord with the present invention, low-frequency pump transducer 12 is operated in a continuous mode at pump frequency $f_p=T_p/2B$, and the sound pressure level on bubble 16 due to pump transducer 12 is known to be:

$$P_{bp} \propto \cos\omega_p\left(t - \frac{r_p}{c}\right)$$

where,
$r_p$=distance between pump transducer 12 and bubble 16, and
c=speed of sound in the surrounding medium 18.

Bubble measuring instrument 10 employs low-frequency pump transducer 12 made by a company of the name of Sonic Concepts. A single, high-frequency, 1" spherically focused, 2.25 MHZ image/receive transducer 14 was used in a preferred embodiment and is made by a company of the name of Panametrics.

The pump frequency may preferably be stepped over the range of bubble resonant frequencies of interest. In one preferred embodiment, the pump transducer was driven by function generator 20, such as a HP33120-A function generator, and high-voltage amplifier 22, such as a Krohn-Hite 7500 Amplifier. At each step, high-frequency 2.25 MHZ image transducer 14 is preferably pulsed at a particular repetition rate via ultrasonic pulser 24, such as a Matec 310 pulser. In a preferred embodiment of the invention, the image frequency is set a priori and is not changed at each step of the pump frequency. The pulse repetition rate of pulser 24 is on the order of 10 kHz and is under software control by the data acquisition system, such as computer 26. Computer is defined as an apparatus that has four types of hardware component: central processing unit(s) (CPU), input device(s), output device(s) and memory. The CPU executes programs (i.e., "software"), which tell the computer what to do. Input and output (I/O) devices allow the computer to communicate with the user (i.e., a person using the computer) and the outside world. There are several kinds of memory—fast, short-term memory (e.g. rapid access memory or "RAM") to hold intermediate results, and slower, long-term memory (e.g. read only memory or "ROM") to hold programs and data between procedures or "jobs". The pulse repetition rate may be adjusted through the virtual panel front of the software shown in FIG. 5 as discussed in more detail hereinafter. Specific restrctions on the selection of the repetition rate and pump frequency in accord with a preferred embodiment of the present invention are discussed below. Thus as stated above, pulse repetition rate and pump frequency are preferably controlled by the computer.

High-frequency image/receive transducer 14 is preferably operated in pulse/echo mode and is driven in pulses or frequency bursts 34 (See FIG. 3) of a sinusoidal signal of duration 1 with each burst 34 being at image frequency $f_i=T_i/2B$. The burst repetition frequency $f_r=1/T_r$. The sound pressure level on bubble 16 due to image transducer 14 is given by:

$$P_{bi} \propto \sum_{n=1}^{\infty} \pi_\tau\left(t - \frac{r_i}{c} - nT_r\right)\cos\omega_i\left(t - \frac{r_i}{c}\right)$$

where,
$r_i$=the distance between image transducer 14, and
c=speed of sound in the surrounding medium 18.

High-frequency image/receive transducer 14 receives a return signal that is preferably amplified by amplifier 28, such as a Matec 605 ultrasonic receive amplifier, and multiplied with multiplier 30 by the reference signal produced by continuous wave oscillator 32 at the image frequency.

The reference signal at the image frequency from oscillator 32 may be given as:

$$X_{R1} = \cos \omega_i t.$$

Two possible cases occur for the received signals. In one case, the bubble acts linearly and the two insonifying signals of pump transducer 12 and image transducer 14 do not interact at the bubble 16 surface. In the second case, bubble 16 acts as a nonlinear mixer. The linear case corresponds to a nonresonant bubble, and the nonlinear case corresponds, to a resonant bubble. For the linear case, the received sound pressure level is:

$$X_{ri\,linear} \propto \sum_{n=1}^{\infty} \pi_r\left(t - \frac{2r_i}{c} - nT_r\right)\cos\omega_i\left(t - \frac{2r_i}{c}\right).$$

The effect of the pumping frequency is neglected because the sensitivity of high-frequency transducer 14 at the much lower pump frequency is nearly zero. For the nonlinear case, bubble 16 acts like a mixer leading to a received signal composed of harmonics of the pump frequency, image frequency, and sideband frequencies of $f_i \pm f_p$, $f_i \pm 2f_p$, etc. If bubble 16 is assumed to be a quadratic mixer, as a first approximation, then the received high-frequency signal from bubble 16 as detected by high-frequency transducer 14 is approximated by:

$$X_{rih\,nonlinear} \propto \sum_{n=1}^{\infty} \pi_r\left(t - \frac{2r_i}{c} - nT_r\right)\cos(\omega_i t - \Phi)\cos(\omega_p t - \phi)$$

where, $$\Phi = \omega_i\left(\frac{2r_i}{c}\right), \quad \text{and} \quad \phi = \omega_p\left(\frac{r_i + r_p}{c}\right)$$

Figure 2:
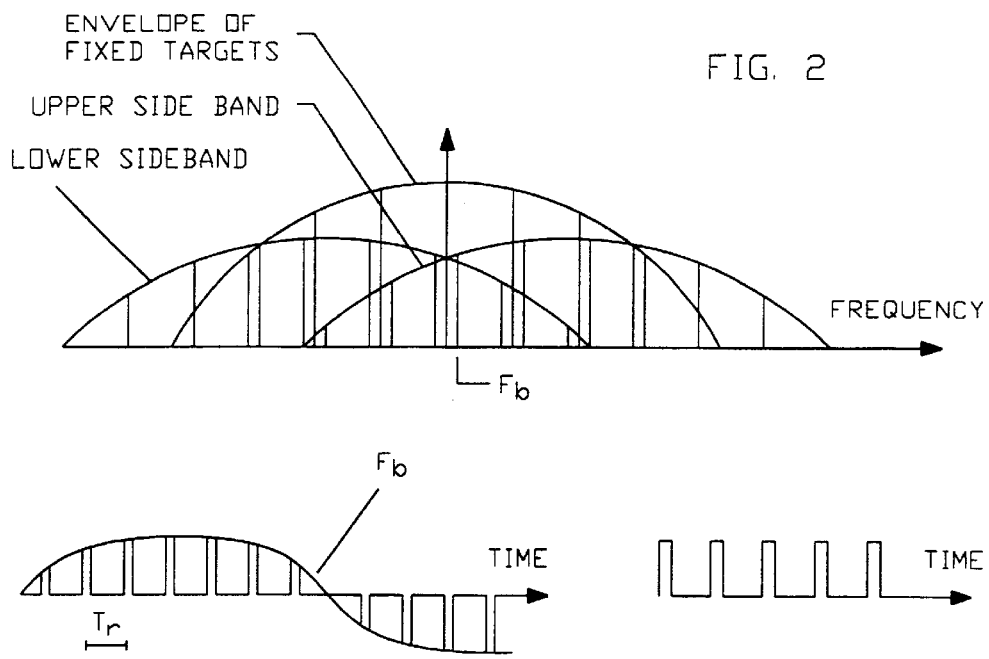
FIG. 2 is a frequency versus amplitude plot that discloses a beat frequency signal in accord with the present invention.

The nonlinear behavior of the bubble creates spectral lines at $f_i \pm f_p$ as indicated in FIG. 2 which is discussed subsequently. The magnitude of these sideband signals is maximum when the pump frequency corresponds to the bubble resonant frequency.

Figure 3:
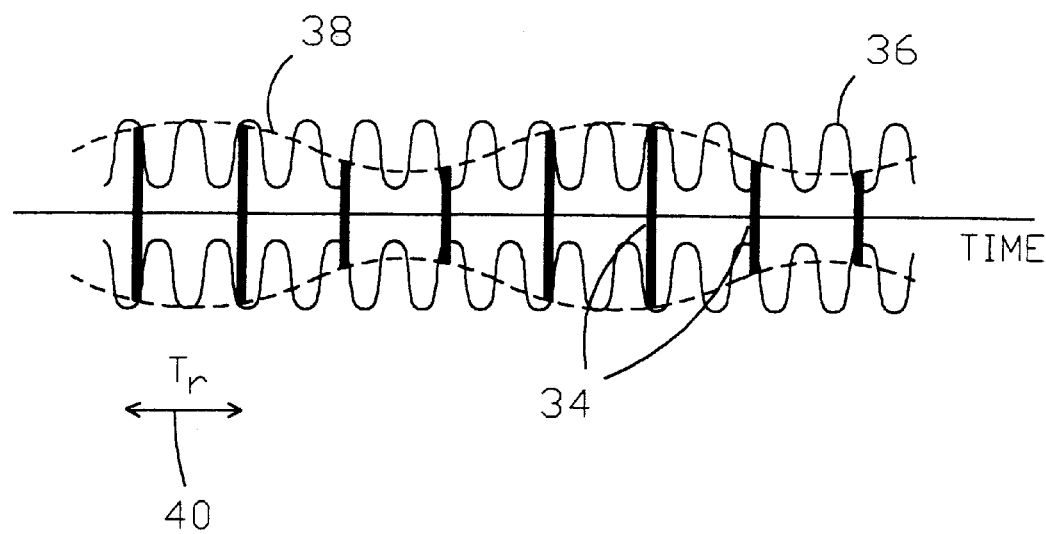
FIG. 3 is a diagram showing relationships between pump frequency, repetition frequency, beat frequency, and image frequency.

In a preferred embodiment of the invention, two restrictions are placed on the repetition frequency $f_r$ of the image signal controlled by computer 26 as effected by pulser 24. The first restriction is to eliminate range ambiguity. For this purpose, the repetition rate is chosen so that:

$$f_r < \frac{c}{(2r_{max})}$$

where $r_{max}$ is the maximum distance between transducers 12 and 14 and the target such as bubble 16. The second restriction is that the repetition rate or frequency $f_r$ cannot be an integer multiple of the pump frequency $f_p$. That is:

$$f_r \neq \frac{f_p}{N}$$

where N is any integer. The basis for this restriction is that a superposition of the nonlinear and linear responses seen above results when $f_r = f_p/N$. In this case, the magnitude of the sidebands is zero. This restriction on the repetition rate or frequency $f_r$ is preferably handled by software of computer 26 which preferably controls the repetition rate or frequency $f_r$ and pump frequency $f_p$ based on the desired bubble size range to be scanned. As the repetition rate for the present invention is preferably chosen significantly lower than the resonant frequency of any bubbles of interest, undersampling occurs resulting in aliasing and a beat signal at beat frequency $f_b$. FIG. 3 shows a representative view of the relationship between some of the signals discussed above with respect to time. Bursts 34 are the imaging signal output from image transducer 14 and are pulses produced at a burst repetition frequency $f_r$ with each burst or pulse being a high-frequency sinusoidal signal at the image frequency $f_i$. The time between each burst 34 as indicated at 40 is $T_r$. Signal 36 is the pump signal at frequency $f_p$. The beat signal 38 is produced in the non-linear case of a resonant bubble at frequency $f_b$. As discussed in more detail hereinafter, the frequency $f_b$ of the beat signal can be controlled by suitable adjustment of $f_p$ and $f_r$.

For nonlinear targets (resonant bubbles), the output of the multiplier 30, which multiplies the received signal and the signal of oscillator 32 for demodulation purposes, is given by:

$$Z_{ib\,nonlinear} \propto \sum_{n=1}^{\infty} \pi_r\left(t - \frac{2r_i}{c} - nT_r\right)\cos(\omega_i t - \Phi)\cos(\omega_p t - \phi)\cos\omega_i t$$

Because the duration $\Pi_r$ is large compared to ½ $f_i$, it is possible to filter out the high-frequency components present at the output of the multiplier 30 by lowpass filter 42 to give a lowpass filter output of:

$$X_{rih\,nonlinear} \propto \sum \pi_r\left(t - \frac{2r_i}{c} - nT_r\right)\cos\Phi\cos(\omega_p t - \phi).$$

For linear targets (nonresonant bubbles) the output of the multiplier 30 is:

$$Z_{1\,linear} \propto \sum_{n=1}^{\infty} \pi_r\left(t - \frac{2r_i}{c} - nT_r\right)\cos(\omega_i t - \Phi)\cos\omega_i t.$$

and the output of lowpass filter 42 is given by:

$$Z_{1\,linear} \propto \sum_{n=1}^{\infty} \pi_r\left(t - \frac{2r_i}{c} - nT_r\right)\cos\Phi.$$

In one preferred embodiment of instrument 10, lowpass filter 42 has a cutoff frequency of 250 kHz. The linear and nonlinear responses of the system after demodulation are depicted in FIG. 2 in the frequency and time domains. For the linear response, we see that the output signal is a low-frequency signal sampled at the repetition frequency $f_r$. As discussed above, because the repetition rate $f_r$ is significantly lower than the resonant frequency of any bubbles of interest, we are undersampling, resulting in aliasing and a beat signal of frequency $f_b$. The frequency $f_b$ of the beat signal is given by:

$$f_b = |Nf_b + f_p|_{min}$$

If $f_p = N f_r$, then the beat frequency $f_b$ is zero, and there is no way to distinguish between linear and nonlinear targets. Consequently, as discussed previously, $f_r$ is chosen such that $f_r \neq f_p/N$. Since both $f_p$ and $f_r$ are independently controlled, this is not a problem. In fact, in accord with the preferred embodiment of the present invention, computer 26 selects the proper pulse repetition rate $f_r$ for each pump frequency $f_p$ to ensure that the beat frequency is always located at a predetermined frequency. This feature allows simplified electronic implementation and is considered highly adantageous.

The beat signal can be extracted from the demodulated, lowpass filtered return signal, i.e., the output of lowpass filter 42, by appropriately range gating and using sample and hold unit 44. Sample and hold unit 44 convolves the sampled signal and the gate function of duration $T_r/2$. The output of sample and hold unit 44 is then lowpass filtered by lowpass filter 46 to eliminate high-frequency spectral components which are artifacts of the signal processing. The signal is also highpass filtered to eliminate low-frequency Doppler effects by highpass filter 48. However, it will also be noted that the Doppler signal is provided on line 50 is the output of lowpass filter 46 and may be viewed on oscilloscope 53. The Doppler signal is used by the software of computer 26 as may be indicated on virtual panel front 58 discussed hereinafter The Doppler signal on line 50 may be used to indicate when a bubble, or other emboli, has passed through the measurement volume.

In accord with a presently preferred embodiment, the pulse or burst repetition rate $f_r$ and the pump frequency $f_p$ are controlled by computer 26 such that the beat signal frequency $f_b$ is at a constant frequency. In a preferred embodiment of instrument 10, 4 kHz was selected. Consequently lowpass filter 46 and highpass filter 48 can be chosen closely around 4 kHz in this embodiment of the invention. For this preferred embodiment, 5 kHz was chosen for lowpass filter 46 and 3 kHz was chosen for highpass filter 48. This design results in excellent noise rejection and selectivity.

Figure 4:
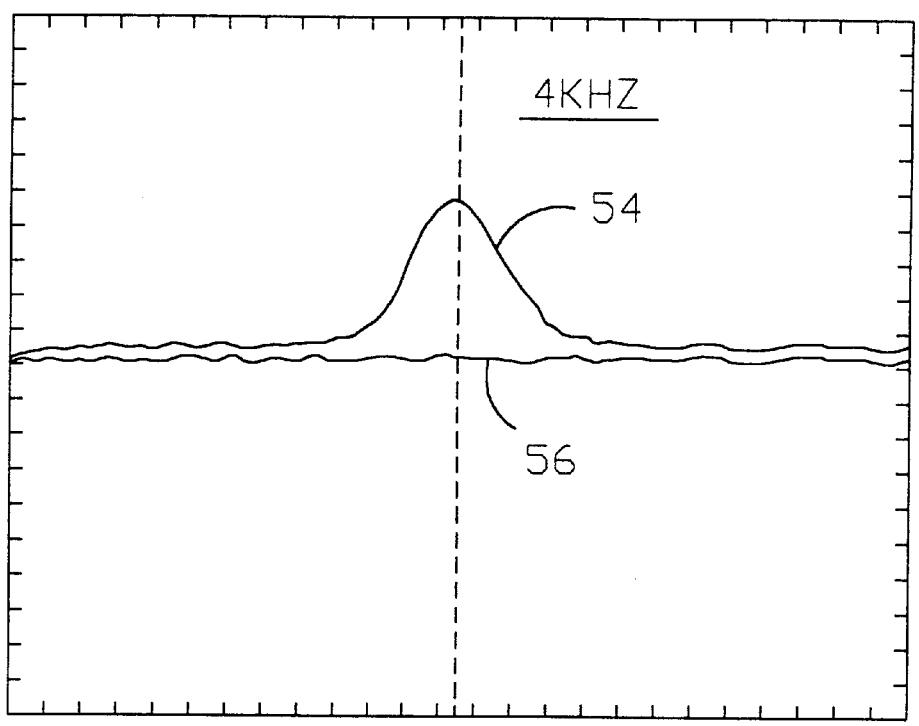
FIG. 4 is a schematic view of a frequency domain beat signal that shows the absence and presence of a beat signal at a preselected frequency related to the absence and presence of a bubble.

FIG. 4 is a frequency domain signal, preferably a fast Fourier transform or FFT signal, that is processed by software from the output data of highpass filter 48. The FFT signal may be viewed in the virtual panel front 58 discussed hereinafter. The raw signal output of highpass filter 48 from which the FFT signal is produced is found on line 52 and may be viewed by oscilloscope 53. FIG. 4 shows the case where a resonant bubble is present with FFT curve 54, which has a center peak at 4 kHz, and for the case where a resonant bubble is not present with FFT curve 56. The amplitude and frequency band for the FFT signal are selectable for determining whether the instrument counts a bubble or not from virtual panel front 58.

Figure 5:
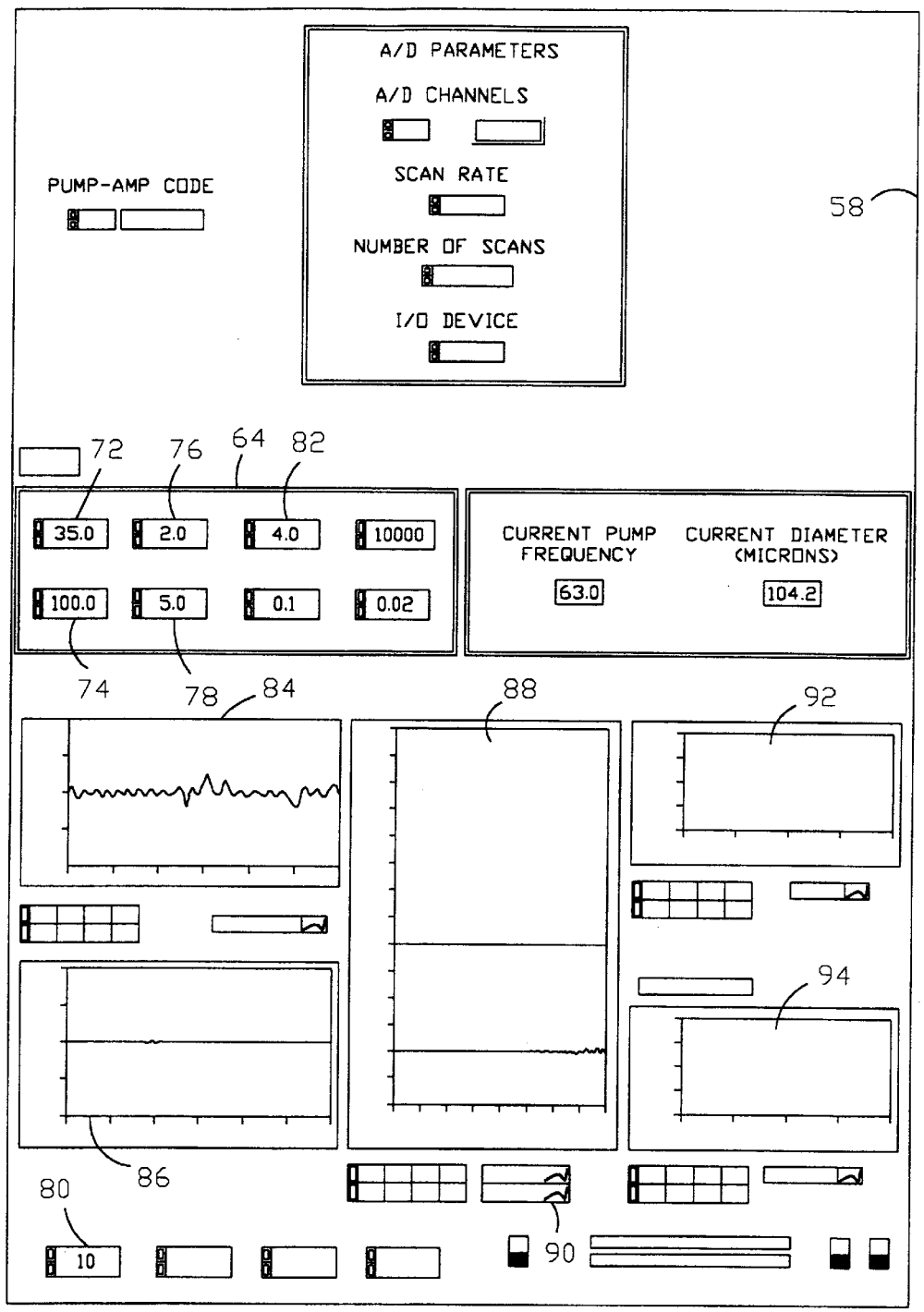
FIG. 5 is a computer screen generated by software showing a virtual instrument front panel for a bubble measuring instrument in accord with the present invention.

FIG. 5 discloses virtual instrument front 58 as might be seen on computer monitor 60 from FIG. 1 in accord with software used for operation of the present invention. With the exception of the setting of sample and hold gate position as operated with elements 44 and delay generator 62 from FIG. 1, and the pump signal amplitude adjustment as per element 22 from FIG. 1, instrument 10 in a preferred embodiment is wholly controlled from virtual front panel 58 so as to be under software control. The software controls of panel 58 include setting the pump sweep frequency range (and hence the bubble sizing range) and step frequency increment, the repetition frequency, and the thresholds on bubble detection. Trigger in line 68 from computer 26 to ultrasonic pulser 24 sets the pulse repetition rate $f_r$. In one preferred embodiment of the invention, bubble sizing instrument 10 is controlled by and data are collected and processed on a Power Macintosh computer with National Instruments data acquisition and GPIB cards.

A signal and hold gate adjust signal is available at line 66 for view on oscilloscope 53 that is used to adjust the gate location at which the amplified, mixed, 250 KHz lowpass filtered output signal from lowpass filter 42 is sampled by sample and hold unit 44. This signal is used in conjunction with output from lowpass filter 42 at line 70 and displayed on oscilloscope 53 with gate signal imposed therewith to set the sample and hold gate location. The sample and hold gate is set such that the peak of the bubble response envelope is held. Because the sampling takes place instantaneously, i.e. at a set time delay from the pulse, it cannot capture the responses of all bubbles that flow through a vessel. Thus, the gate is preferably set at the position of the greatest amount of bubble activity, which is usually the center of the vessel.

The pump amplitude may be preferably set using high voltage amplifier 22, which may be a Krohn-Hite 7500 unit. The amplitude should be set high enough to resonate the bubbles. However, the pump transducer signal can couple with that of the image transducer 14 if its amplitude is set too high.

Referring to FIG. 5, in a preferred embodiment, the user determines the range of bubble sizes to interrogate by setting the start, stop, and step frequencies on middle left box 64 of the control panel such as in the present example where start frequency is at box 72, end frequency at box 74 and increment or step frequency at box 76. As the pump transducer sweeps through this frequency range, only one bubble size is interrogated at a time. The Number of FFT's per Frequency Increment box 78 determines the time spent at each frequency. Thus, there is a tradeoff between sweeping through the bubble size range quickly by jumping over bubble sizes and sweeping through slowly, interrogating many more bubble sizes within the range.

The repetition rate is input at the lower left corner of the control panel at box 80 and sets the rate at which the bubbles are pulsed with the imaging signal. This is a nominal frequency such as 10 kHz or a range from about 4 kHz to 12 kHz as the actual repetition rate is calculated and varies around this frequency. In bubble sizing experiments, we have found that noise in the bubble sizing signal could be minimized by adjusting the repetition rate to some optimum value, which was suited for that particular acoustic environment. As discussed above, the repetition rate $f_r$ is used to control beat frequency $f_b$ which is optimally set at 4 kHz for the present setup as indicated at 82.

Five plots are displayed on screens or windows on the control panel. The two on the left side are real-time plots of the Doppler signal at 84 and the Bubble Data signal at 86. The Doppler signal gives a visual indication of the presence of bubbles. It is nominally flat when no bubbles pass by the measurement volume and fluctuates in amplitude when bubbles are present. The bubble data signal is the final output of the signal processing electronics at line 52. From this signal, the software calculates a frequency domain signal or FFT signal such as shown in FIG. 4 and displays it in center plot 88. Bubbles of a given size are deemed detected when the amplitude of the FFT signal exceeds the amplitude FFT Threshold setting and occurs at a frequency within the Threshold Frequency Span. These two thresholds settings are located in the middle left box on the control panel at 90. The two plots on the right-hand side of the control panel display the bubble sizing results. The top right plot at 92 displays the real-time histogram of whether a bubble of a given size has been detected, and the plot beneath it at 94 displays the bubble sizing histogram from the last sweep.

While running a bubble sizing test, the data may be concurrently written to a file using the inputs on the lower right side of the control panel. Prior to running a test, the user inputs a file name and enables the Save File switch.

Various means were used for bubble production. Hydrolysis techniques (not shown) easily provides large numbers of small (~20 $\mu$m diameter) bubbles. However, it is difficult to produce bubbles much larger than 100 $\mu$m diameter via this technique. The hydrolysis technique also tends to produce a dense cloud with a broad distribution of bubble sizes. Consequently, an alternative approach was required to produce bubbles over the entire 40 $\mu$m to 400 $\mu$m diameter size range of interest here with both narrow and wide size distributions as required.

Figure 13:
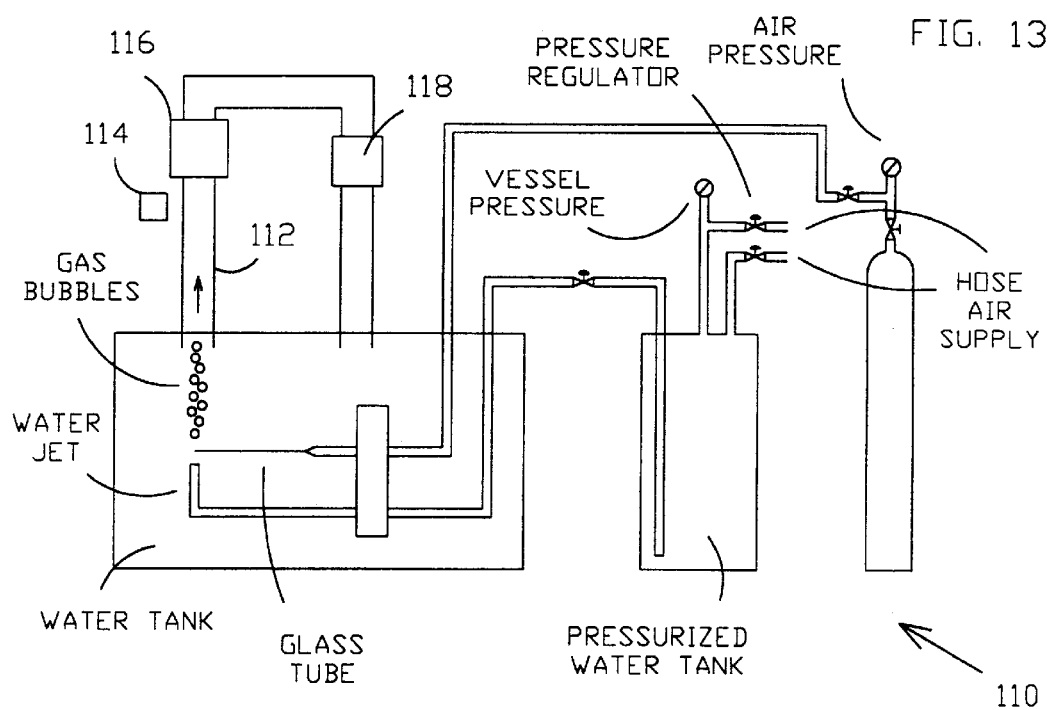
FIG. 13 provides an embodiment of one bubble producing system in accord with the present invention.

Using a bubble producing system such as system 110 shown in FIG. 13, bubbles were also produced by blowing helium or air through a small drawn capillary tube. To control the size of the bubbles, a water jet was directed upward at the tip of the capillary tube. By controlling the supply pressure to the capillary tube and the jet velocity, we were able to control the bubble size and the number of bubbles produced. We were often able to produce bubbles on the order of 20 $\mu$m in diameter with this technique, and reliably we could produce them down to the 30 $\mu$m to 40 $\mu$m in diameter. In the 60 $\mu$m diameter range and above, we were able to produce relatively mono-disperse bubble clouds with a narrow size distributions. When smaller bubble sizes were produced, the distributions tended to be broader.

Figure 6:
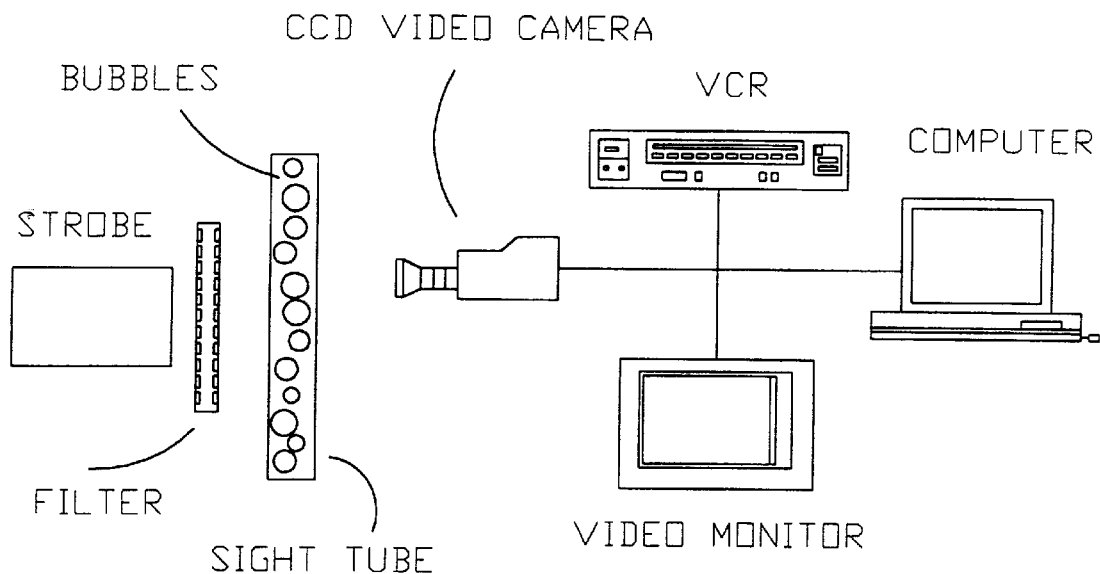
FIG. 6 is a block diagram schematic of a video microscopy system for independently counting and sizing bubbles to verify results from the bubble measuring instrument of the present invention.

Bubbles were sized using video microscopy and image analysis software. The setup is shown schematically in FIG. 6. The system consists of a CCD video camera, 50× fixed lens, monitor, strobe light, light filter, and computer runnina NIH Image software. The resolution of the system based on the resulting pixel size is approximately 4 $\mu$m. Video data is collected on a Power Macintosh computer with its built in frame grabbing capability. Using software, such as NIH Image Software, the bubble sizes are measured on a number of statistically independent frames (e.g., the same bubble was never measured twice in two different frames) to determine the size distribution for a given set up of the bubble blower.

Figure 7:
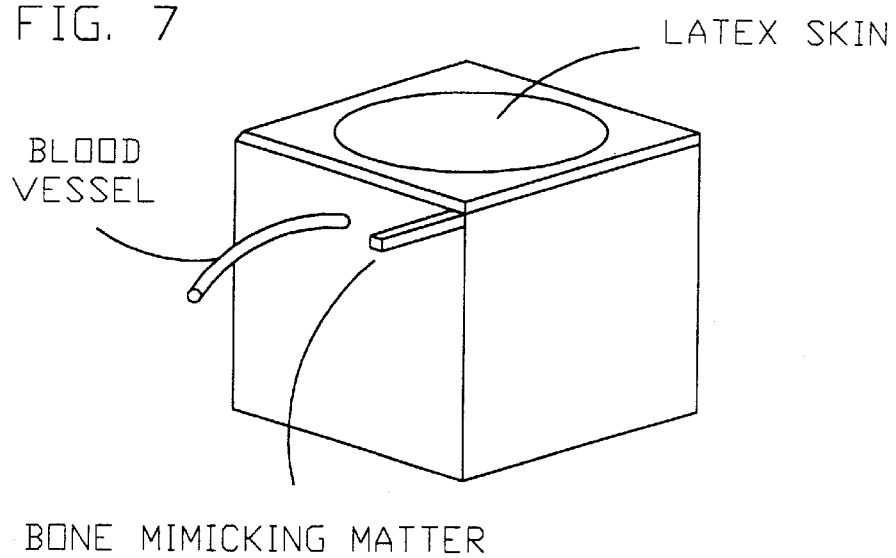
FIG. 7 is an isometric view of a phantom tissue assembly for modeling anatomy including skin, tissue, blood flow, and bone to permit simulation of an in-vivo measurement environment.

Initial work was conducted in a large tank with free-floating bubbles. However, to more accurately model the in-vivo testing situation in accord with the objectives of the present invention, several tissue phantoms were constructed for use in connection with the video microscopy system of FIG. 6 and the bubble generating apparatus of FIG. 13. Tissue phantoms, an example of which is shown in FIG. 7, were constructed modeling both the anatomy of the upper human leg and the inner, upper portion of a canine rear leg. The human leg tissue phantom consisted of a Plexiglas support structure, a tissue mimicking gel, and skin mimicking polymer covering. A Plexiglas rod was embedded in the phantom to model the femur. A tubing material is preferably used to model the femoral vasculature having ultrasonic properties similar to those of actual blood vessels as known to those of skill in the art. Coupling to the vessel was provided for by filling the phantom with water, and the skin was modeled with a thin latex sheet. The bone behind the vessel was modeled with PVC plastic. All of the in-vitro test results presented herein were obtained with the canine tissue phantom since this was most representative of our initial in-vivo application.

Bubbles were produced in bubble generating apparatus 110 in an open water tank as indicated in FIG. 13 for most of the testing over the range of bubbles from 40 $\mu$m to 400 $\mu$m. For bubbles on the order of 20 $\mu$m and smaller, a hydrolysis system (not shown) was found to be more reliable. However, apparatus 110 was satisfactory for producing bubbles over the range of sizes of initial interest.

It will be noted that generating bubbles of different sizes was a difficult task. Glass tubes of appropriate sizes were drawing and used and it was found that jagged end tubes were more reliable than polished or smooth ending glass tubes. For certain ranges of bubbles, significant trial and error was required to produce the correct size glass tube. Compressed air was directed through the glass tubes and also used to produce a water jet. By controlling the supply pressure to the capillary glass tube and the jet pressure, the bubble size and number of bubbles produced could be controlled. The bubbles were entrained in an upward flow through sight tube 112 such as the sight tube of FIG. 6, where they could be sized optically. The bubbles were then directed through the simulated vasculature 116, such as that shown in FIG. 7. To provide a life-like in-vitro simulation, the flow was driven by peristaltic pump 118 at velocities in the range of two cm/sec to ten cm/sec to mimic heart flow.

Figure 10:
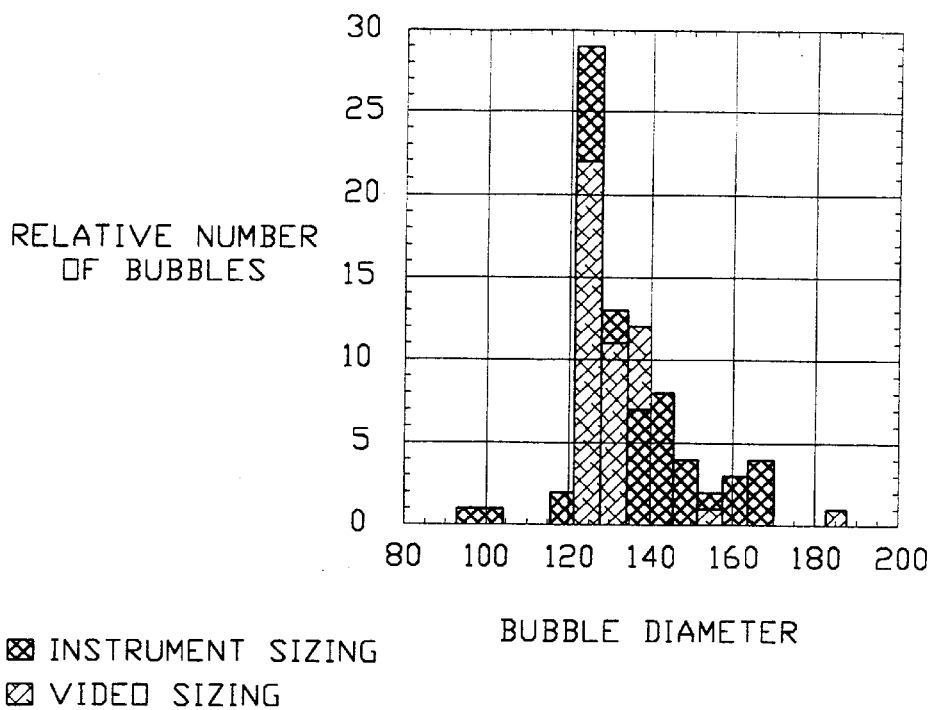
FIG. 10 is a comparison of video microscopy analysis of bubble population to that of the bubble measuring instrument in accord with the present invention for a setting of 120 to 160 micrometers for bubble size range to be measured.
Figure 11:
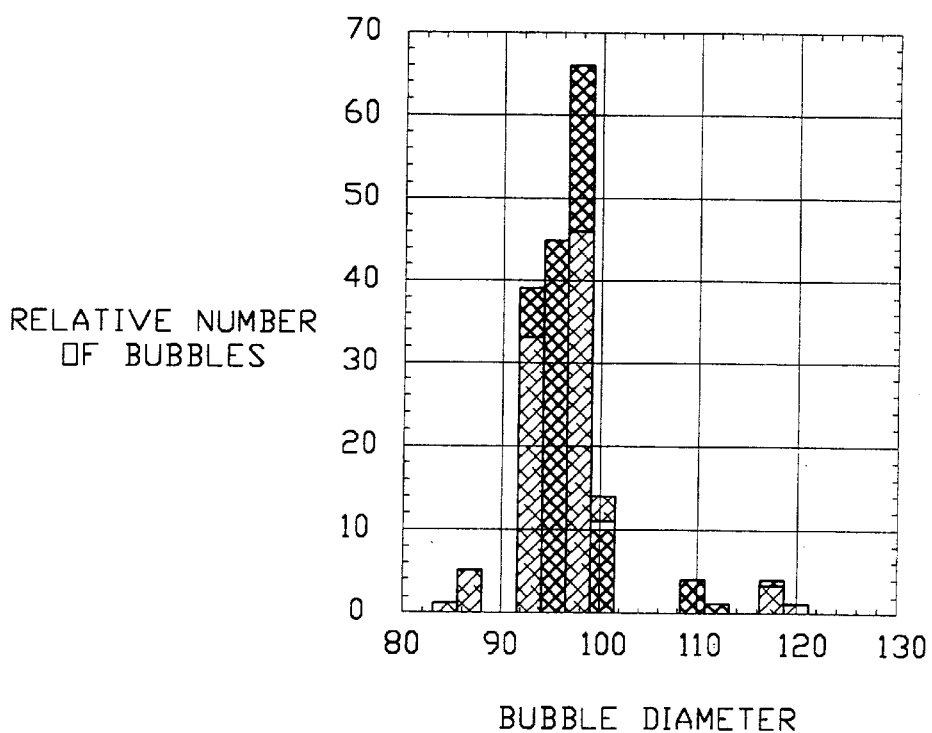
FIG. 11 is a comparison of video microscopy analysis of bubble population to that of the bubble measuring instrument in accord with the present invention for a setting of 97 micrometers for the bubble size range to be measured.

An objective of the present invention was to show that the ultrasonic bubble sizing instrument produced results which could be confirmed by independent video microscopy. As such, the main result of the in-vitro testing is a series of histogram plots comparing the output of the bubble sizing instrument to the size distributions measured by video microscopy. Representative examples of results for sample bubble size distributions are shown in FIG. 10 and FIG. 11. Intermediate results such as RF return signals from the measurement volume are shown in FIG. 8 and FIG. 9 and the spectral decompositions of the processed return signals showing the beat frequency from bubbles, and the lack of a beat frequency for non-resonant bubbles in FIG. 4 are also presented.

Figure 8:
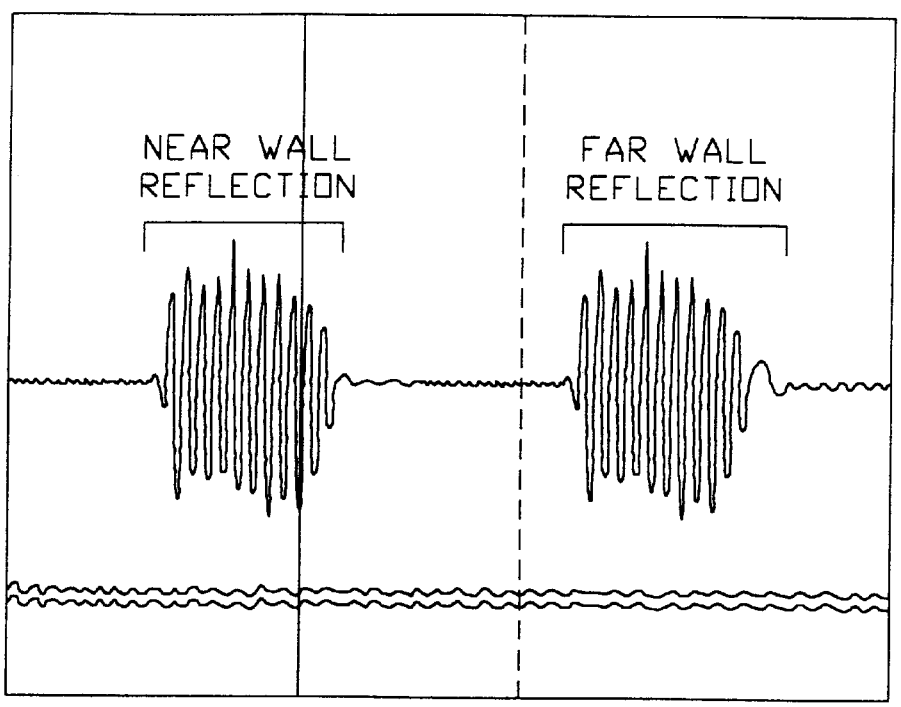
FIG. 8 is a schematic view of an oscilloscope screen showing a high-frequency return signal from a measurement volume wherein no bubble is present.
Figure 9:
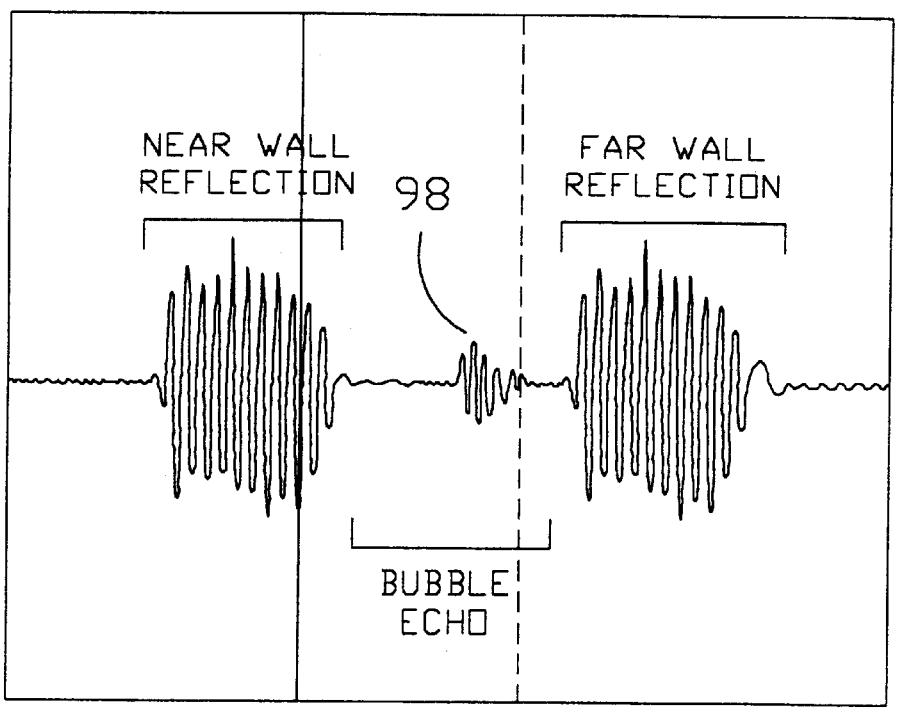
FIG. 9 is a schematic view of an oscilloscope screen showing a high-frequency return signal from a measurement volume wherein a bubble is present.

In more detail, FIG. 8 and FIG. 9 illustrates the high-frequency return signals from the measurement volume without and with a bubble present in the volume as might be seen on oscilloscope 53 selecting the signal on line 96 using a tissue phantom such as that of FIG. 7. Bubble echo 98 is seen in FIG. 9. The results are essentially independent of the bubble size although larger bubbles tend to create echoes with larger magnitude. FIG. 8 and FIG. 9 clearly illustrate the reflections from the near and far walls of the simulated blood vessel. The reflections also provide a convenient means for aligning high-frequency transducer 14 in vitro and in vivo.

FIG. 4 presents the spectrum of processed return signals 54 and 56 from the high-frequency image transducer as discussed previously. The plot is centered at 4 kHz since the beat frequency $f_b$ is preferably selected as 4 kHz and the presence of the beat signal at this frequency indicates there is a resonant bubble. As discussed above, the pulse repetition rate $f_r$ and pump frequency $f_p$ are preferably selected to produce this beat frequency. This feature of the invention allows us to threshold over a single small frequency range, reducing the noise and improving the selectivity of the instrument. FIG. 4 clearly shows a return signal 54 with a strong 4 kHz component, corresponding to a resonant bubble, and another return signal 56 without a strong 4 kHz component, corresponding to the absence of a resonant bubble. As discussed above, such signals may be displayed at 88 of virtual instrument panel 58 with the amplitude and frequency cut off ranges selected at 90 so instrument 10 will count the signal as a bubble or not.

FIG. 10 and FIG. 11 present several comparisons of the bubble size distributions as determined by the bubble sizing instrument and the independent video microscopy sizing technique. In general tests, it was found that the comparison between the size distributions between the two techniques is superb.

Extending the range of the instrument above 200 $\mu$m requires the use of another pump transducer which can operate at frequencies below 30 kHz. Instrument 10 was successfully used with such a transducer, but because these large bubbles are not likely to be of much interest in DCS research not much work was done in this range. Extending the range of the instrument below 30 μm bubble diameters is also possible by using another pump transducer which can operate at frequencies above 200 kHz. Based on the signal-to-noise ratio we observed at 30 μm bubble diameters, we have every reason to believe that with a suitable pump transducer, it would be possible to size bubbles much smaller than 30 μm with instrument 10. Instrument 10 works very well even if the bubble size distribution is broad.

Figure 12:
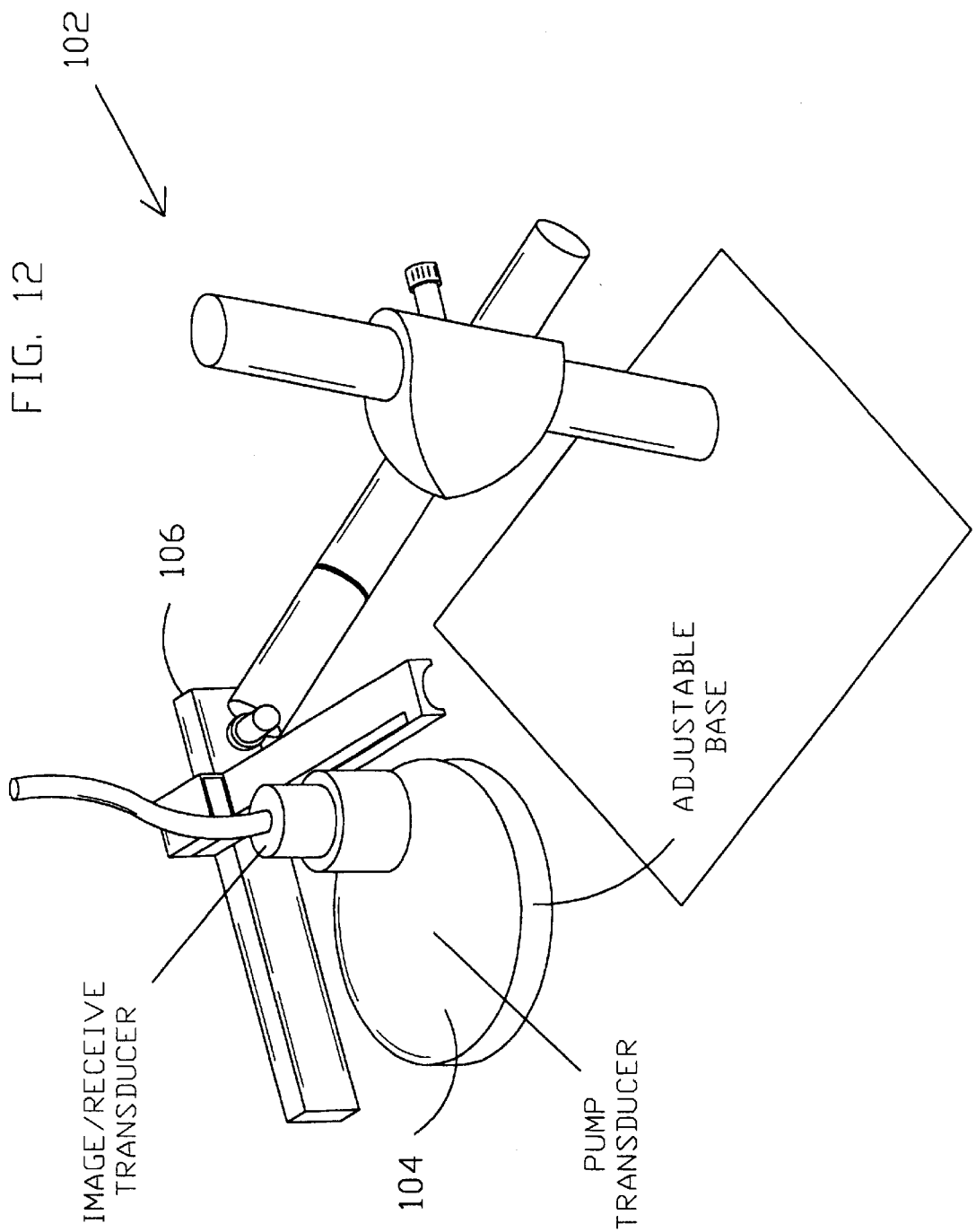
FIG. 12 is an isometric view of an in-vivo transducer fixture in accord with the present invention.

For in-vivo testing a fixture, such as fixture 102, is preferably used to hold the imaging and pump transducers as indicated in FIG. 12. Fixture 102 allows for the independent height adjustment of the image transducer so that it can be optimally positioned at its focal distance. The fixture also allows for an independent angle adjustment on the pump transducer. However, the pump transducer is relatively omni-directional, and its alignment is not critical. Transducer holder 104 can be packed with ultrasonic coupling gel, and there is an adjustable base portion which allows one to alter the height of both transducers and contain the coupling gel. Transducer holder 104 is held by a multi-degree-of-freedom support arm 106. The preliminary results provided a good demonstration of the device in vivo, which was the primary objective of this activity. Because fixture 102 is designed for external use, other design criteria would be required for use internally. The optimum focusing distance for the image transducer of a presently preferred embodiment is 0.125 inches. Pump transducer 12 is preferably directed slightly upstream of the focusing point for image transducer 14 so as to be resonating bubbles before the point where they are insonified by image transducer 14.

It will be understood that numerous variations of the invention may be made. Several variations are listed below but are not considered to be exhaustive of the possible variations but simply show examples.

As mentioned above, transducer fixture 102 was intended for the external femoral vein location and works well there. However, a smaller, more compact fixture could easily be fabricated if desired for internal use as may be desired for testing purposes. A different, more flexible support arm would be required for internal purposes as well.

General testing could determine the best type of coupling such as whether or not a coupling gel bag should be used instead of free standing gel. The get bags might prove to be a better approach in that there will likely be less entrapped air bubbles, and might also be a lot neater.

A Doppler audio signal could be used to aid alignment. This would be a relatively straightforward enhancement, because a pseudo-Doppler signal is a byproduct of the signal processing. This would likely be very helpful, especially if it would allow the user to hear the blood flowing in a vessel.

It would be desirable to extend bubble size range below 30 μm diameter bubbles. The original target lower bound for the range of the bubble sizing instrument was 40 μm diameter bubbles. We exceeded this target and demonstrated operation down to 30 μm diameter bubbles. Preliminary in-vivo test results indicate that there are DCS bubbles with 30 μm diameter. Results at 30 μm diameter give us every indication that an appropriate higher frequency pump transducer is all that is needed along with in-vitro testing to verify the operation of the instrument at smaller bubble diameters.

It would also be desirable to build an artery/vein cuff. DCS research would be aided by an artery or vein cuff that would aid alignment of the system directly on a desired excised vessel such as the vena cava or pulmonary artery.

It would also be desirable to include a transesophogeal probe. It would be possible to take a standard transesophogeal ultrasound probe and integrate the bubble sizing transducers into it and the ultrasound machine so that one could easily target a specific vessel or region of tissue using the ultrasound machine. A reticule would be used to select the target volume on the ultrasound image as is done now for the Doppler on a standard ultrasound system.

The pulmonary artery is of significant interest in DCS research and in-suit monitoring of astronauts for DCS precursor bubbles. Therefore, instrument 10 could be applied to monitoring of DCS bubbles in the pulmonary artery.

Instrument 10 could also be modified for use transcutaneously. The concepts of instrument 10 may also be suitable for a transcatheter operation with appropriate transducers and adjustments to frequencies based on the limitations of such transducers.

Artificial heart valves are known to sometimes generate emboli. It is not known if these emboli are thrombic or gaseous emboli produced by cavitation. Consequently, the bubble monitoring instrument could be used to classify these emboli.

The formation of the extravascular bubbles is of significant interest to DCS researchers. The bubble sizing instrument disclosed herein could very likely be applied to the study of extravascular bubbles. Although it has not been specifically tested in this scenario, it is likely that extravascular bubbles will display resonant behavior very similar to that of intravascular bubbles. Since the primary interest in extravascular bubble research is to determine whether or not the bubbles are forming, it is not important that the resonant behavior be exactly predicted or known, just that the bubbles do resonate so that they can be detected. Existing ultrasound imaging techniques do not reveal their presence.

In a brief summary, the general procedure for running the instrument is to power up the electronics and start the software, align the transducers, set the sample and hold gate position, set the pump amplitude, adjust the software controls, and finally take bubble sizing data. With the exception of the setting of the sample and hold gate position and the pump amplitude discussed herein before, a preferred embodiment of instrument 10 is wholly controlled via inputs on the virtual front panel 58 shown in FIG. 5. A range of bubble sizes to be investigated is selected. The time spent surveying the range is selected. The relative frequency band and amplitude of the FFT signal is selected to indicate the presence of a bubble. Numerous other parameters may also be selected depending on the particular investigation. The information is then acquired and can be displayed to indicate quantities of bubbles and their relative sizes which were detected in the measurement volume.

Thus, while the preferred embodiment of the bubble monitoring apparatus and methods are disclosed in accord with the law requiring disclosure of the presently preferred embodiment of the invention, other embodiments of the disclosed concepts may also be used. Therefore, the foregoing disclosure and description of the invention are illustrative and explanatory thereof, and various changes in the method steps and also the details of the apparatus may be made within the scope of the appended claims without departing from the spirit of the invention.

What is claimed is:

1. A video bubble sizing test system for performing dynamic bubble measurements, comprising:
   a video camera with software and associated memory for capturing a set of video images of a group of bubbles as said group of bubbles moves along a fluid flowpath over a time interval, which video camera includes software and memory means for measuring bubble sizes in comparison to a known reference size or scale, a sight tube extending along said fluid flowpath and containing said group of moving bubbles, and a strobe for producing a plurality of separate video frames that show said bubbles resolved and separated over said time interval so as to facilitate said video bubble sizing.

2. The video bubble sizing test system of claim 1, further comprising:

a video monitor for viewing said separate video frames with bubbles therein.

3. The video bubble sizing test system of claim 1, further comprising:

said software being operable for providing statistically independent frames such that the same bubble is not measured twice in said separate video frames.

4. The video bubble sizing test system of claim 1, further comprising:

a bubble generator operable for selectively generating bubbles having varying diameters.

5. The video bubble sizing test system of claim 4, wherein said bubble generator is operable for generating bubbles at least over the range of 40 micrometers to 200 micrometers.

6. The video bubble sizing test system of claim 1, further comprising:

a tissue phantom through which said bubbles flow.

7. The video bubble sizing test system of claim 6, further comprising:

said ultransonic bubble monitor being positioned adjacent said tissue phantom for monitoring bubbles in said tissue phantom.

8. The video bubble sizing test system of claim 1, further comprising:

a peristaltic pump for pumping fluid so as to mimic blood flow.

9. A bubble diameter measuring apparatus for performing dynamic bubble measurements, comprising:

a controller device which is electrically connected to a bubble measuring detector, where said controller device is configured and operated to generate a set of control software that varies in response to an output from said bubble measuring detector, and a software-controlled computer with an associated memory that is operable for producing a virtual instrument on a computer monitor; and a selection indicator on said virtual instrument for selecting a range of bubble diameters to be examined by said bubble measuring detector and software-controlled computer.

10. The bubble measuring apparatus of claim 9, further comprising:

a screen for said virtual instrument for displaying a frequency domain signal related to a particular size bubble.

11. The bubble measuring apparatus of claim 9, further comprising:

one or more selection indicators for selecting an amplitude and frequency range of said time domain signal to thereby determine whether a bubble is detected or not.

12. The bubble measuring apparatus of claim 10, further comprising:

a second screen for said virtual instrument with the capability of forming a virtual image for displaying a Doppler signal.

13. The bubble measuring apparatus of claim 9, further comprising:

a selection indicator on said virtual instrument for selecting a frequency increment related to said range of bubble diameters to be examined.

14. A bubble measuring apparatus, comprising:

a software controlled computer operable for producing a virtual instrument on a computer monitor;

a selection indicator on said virtual instrument for selecting a range of bubble diameters to be examined;

a screen for said virtual instrument for displaying a frequency domain signal related to a particular bubble size; and software for generating summary charts that display the number of bubbles detected over a selected range of bubble diameters.

* * * * *